(12) United States Patent
Leeming et al.

(10) Patent No.: US 6,270,786 B1
(45) Date of Patent: Aug. 7, 2001

(54) METHOD OF PREPARING A BIOCIDAL MATERIAL

(75) Inventors: Karen Leeming, Bushey; Christopher P. Moore, Rayners Lane, both of (GB)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/113,046

(22) Filed: Jul. 9, 1998

(51) Int. Cl.[7] ............................... A01N 25/08; A01N 25/10
(52) U.S. Cl. ............................................. 424/409; 424/405
(58) Field of Search ....................................... 424/405, 409

(56) References Cited

U.S. PATENT DOCUMENTS

| 5,322,834 | 6/1994 | Hsu | 504/156 |
| 5,648,086 | * 7/1997 | Redlich et al. | 424/409 |
| 5,703,105 | * 12/1997 | Redlich et al. | 514/372 |
| 6,059,980 | * 5/2000 | Leeming et al. | 210/755 |

FOREIGN PATENT DOCUMENTS

| 106563 | * 4/1984 | (EP) . | |
| 0 733 304A | 9/1996 | (EP) | A01N/25/26 |

* cited by examiner

Primary Examiner—Robert H. Harrison

(57) ABSTRACT

A method of preparing a biocidal material comprises taking a biocidal material comprising a biocide having a log P value of at least 1.5 immobilized by hydrophobic exclusion on a support having a hydrophobic surface which has been used for inhibiting microbial growth in an aqueous medium, extracting the biocide from the biocidal material with a solvent, and immobilizing the extracted biocide by hydrophobic exclusion on a support having a hydrophobic surface.

10 Claims, 3 Drawing Sheets

METHOD OF PREPARING A BIOCIDAL MATERIAL

FIELD OF THE INVENTION

The invention relates to the preparation of a biocidal material. More particularly, it relates to the regeneration and reuse of immobilized biocide from an existing biocidal material.

BACKGROUND OF THE INVENTION

Microbial growth occurs in many systems in which aqueous media such as water, aqueous solutions and aqueous dispersions are employed.

For example, significant biofouling can occur in many areas of photoprocessing systems and, in particular, where low flow rate washes and water recycling is used. The problem may be overcome by adding biocides to the wash water tanks when bacterial biofilm formation becomes evident visually. However at this point the biocides may not work and even at quite high concentrations are not particularly effective because the bacteria have attached to surfaces to form colonies which have built up in layers. Hence, any biocide in solution can only reach the outer biofilm layer and not the inner layers of the biofilm which are protected. Furthermore, widespread use of such biocides is not desirable because they are relatively expensive and toxic chemicals which require specialised disposal to protect the environment.

It is known that in addition to being used up in the process of inhibiting the growth of microorganisms, biocides tend to degenerate and lose their activity through prolonged contact with the aqueous medium being treated.

EP-A-0 733 304 describes a biocidal material comprising a biocide immobilized on a support characterised in that the biocide has a log P value of at least 1.5, the support has a hydrophobic surface and the biocide is immobilized on the hydrophobic surface by hydrophobic exclusion. The support may take the form of polymer beads which may be held in a container having an inlet and an outlet so that the aqueous medium to be treated can be contacted with the beads by passing it through the container. An advantage of the material is that the biocide remains attached to the support. The material may be used to inhibit microbial growth in the wash water or other solutions used in a photoprocessor.

PROBLEM TO BE SOLVED BY THE INVENTION

After prolonged use, the biocidal material comprising immobilized biocide becomes exhausted and needs to be replaced. It would be economically and environmentally advantageous if further use could be made of the material without disposing of it and replacing it with completely new material.

It has been found unexpectedly that significant amounts of active biocide can be removed from the material by solvent extraction and the extracted biocide re-used to provide new biocidal material.

SUMMARY OF THE INVNETION

The invention provides a method of preparing a biocidal material which comprises taking a biocidal material comprising a biocide having a log P value of at least 1.5 immobilized by hydrophobic exclusion on a support having a hydrophobic surface which has been used for inhibiting microbial growth in an aqueous medium, extracting biocide from the biocidal material with a solvent, and immobilising the extracted biocide by hydrophobic exclusion on a support having a hydrophobic surface.

ADVANTAGEOUS EFFECT OF THE INVENTION

A significant amount of active biocide can be recovered from used material and re-used.

DETAILED DESCRIPTION OF THE INVENTION

Figure 1:
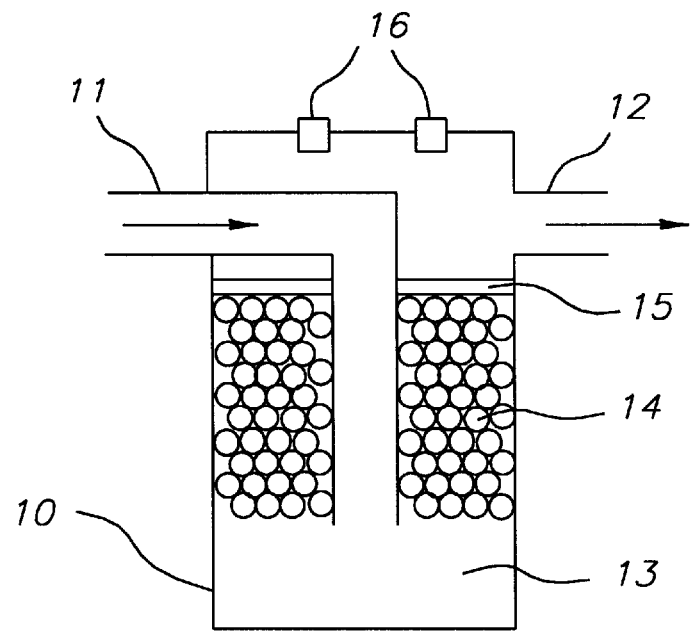
FIG. 1 is a schematic representation of a device holding biocidal material.

Biocides for use in the invention have a log P value of at least 1.5 wherein P represents the partition coefficient between n-octanol and water defined as follows $$P = \frac{[biocide]_{octanol}}{[biocide]_{water}}$$

Log P is a well known term used in literature on biocides. As used herein, it provides a measure of the hydrophobicity of the biocide.

Biocides which may be employed include any known biocide meeting the hydrophobicity requirement or a known biocide which has been hydrophobically modified to meet the requirement.

Suitable types of biocide include those described in "Microbiocides for the Protection of Materials", W. Paulus, published by Chapman Hall, 1993. They are agents capable of killing or inhibiting the multiplication of microorganisms such as bacteria, yeasts, fungi, algae and lichens. Examples include heterocyclic N,S compounds, compounds with activated halogen groups and quaternary ammonium salts.

Preferred biocides include those currently employed in the treatment of photoprocessing systems e.g. isothiazolinones.

Examples of isothiazolinone biocides are those having the structure wherein
R represents hydrogen, alkyl, aryl, alkaryl and aralkyl; and,
$R^1$ and $R^2$ independently represent hydrogen, halogen, alkyl, or $R^1$ and $R^2$ taken together represent the atoms necessary to complete a fused carbocyclic ring, preferably a 5- or 6-membered ring e.g. a benzene ring;

provided that R, R¹ and R² are chosen so that the log P value of the compound is at least 1.5.

Preferred biocides include those having the following structures:

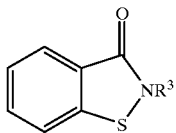

wherein R³ is an alkyl group having from 4 to 20 carbon atoms or an aryl group having from 6 to 20 carbon atoms;

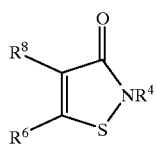

wherein $R^5$ and $R^6$ are selected from hydrogen and halogen, and $R^4$ is an alkyl group having from 5 to 20 carbon atoms; and,

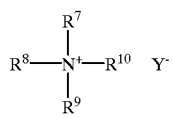

wherein each of $R^7$, $R^8$ and $R^9$ is hydrogen or an alkyl group providing a total of from 2 to 20 carbon atoms; $R^{10}$ is substituted or unsubstituted alkyl or aryl e.g. phenoxyethyl; and, Y is any suitable counter anion e.g. halide.

Specific examples of commercially available isothiazolinone biocides include Proxel™ (manufactured by Zeneca):

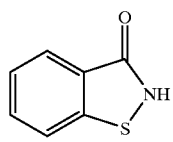

Promexal™ (manufactured by Zeneca):

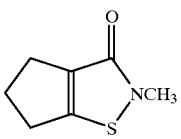

Kathon™ LX (manufactured by Rohm and Haas):

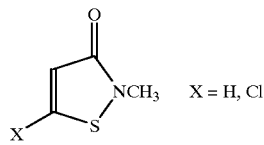

Other commercially available biocides are:

Bronopol™ (manufactured by Boots):

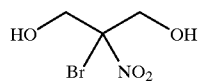

Domiphen™ bromide (manufactured by Ciba-Geigy):

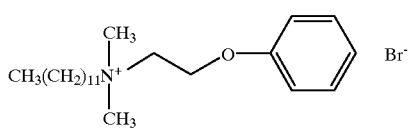

Vantocil™ (manufactured by Zeneca):

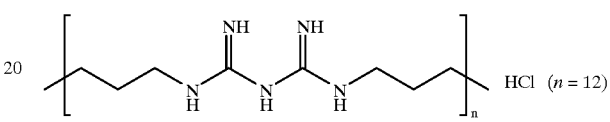

Densil S™ (manufactured by Zeneca):

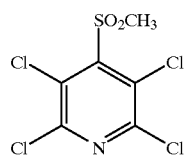

Biocides which are hydrophobically modified Proxel™ and Kathon™ LX have been prepared having the following structures:

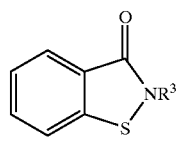

$R^3 = $ —(CH$_2$)$_7$CH$_3$ (Compound 1)
$R^3 = $ —(CH$_2$)$_{15}$CH$_3$ (Compound 2)

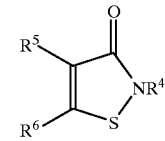

$R^4 = $ —(CH$_2$)$_7$CH$_3$, $R^5 = $ H, $R^6 = $ Cl (Compound 3)
$R^4 = $ —(CH$_2$)$_{17}$CH$_3$, $R^5 = $ H, $R^6 = $ Cl (Compound 4)
$R^4 = $ —(CH$_2$)$_7$CH$_3$, $R^5 = $ H, $R^6 = $ H (Compound 5)
$R^4 = $ —(CH$_2$)$_7$CH$_3$, $R^5 = $ Cl, $R^6 = $ Cl (Compound 6)

Many commercially available biocides are soluble in aqueous media and an increase in their hydrophobicity is required to render them suitable for use in the invention.

It is essential that biocides having a log P of at least 1.5 are used in the invention. Biocides having a log P less than 1.5 can become detached from the support and contaminate the aqueous medium.

Hydrophobic polymers suitable for use as support materials include any inert, water insoluble polymers.

Examples of suitable polymers are ethenic polymers including polyolefins, polystyrene, polyvinyl chloride, polyvinyl acetate and acrylic polymers; and polymers formed by condensation reactions including polyesters, polyamides, polyurethanes, polyethers, epoxy resins, amino resins and phenol-aldehyde resins.

Specific examples of support materials are Amberlite™ XAD-4 and XAD-2 resin beads which are both highly porous, cross-linked polystyrene.

The support may take a variety of forms e.g. particulate, sheet or fibre. It may be porous or non-porous.

The biocide is immobilized on the support by a hydrophobic exclusion mechanism. Immobilisation may be carried out by addition of the dry support e.g. a resin to a solution of the biocide in an organic solvent e.g. tetrahydrofuran (THF), followed by slow addition of a similar volume of water. As the volume fraction of water increases, the biocide and the support associate to exclude water by the well known hydrophobic effect. The support may be left in contact with the solution for a period of time e.g. 18 hours allowing most of the organic solvent to evaporate. Subsequent drying of the support leaves the biocide adsorbed thereto.

Alternatively, immobilization may be carried out by adding water to the dry support, contacting the support with a solution of the biocide in an organic solvent e.g. heptane, and removing the solvent e.g. by evaporation under reduced pressure.

The hydrophobic exclusion mechanism by which the biocide is immobilized is a reversible physisorption wherein the biocide is hydrophobically bound to the support.

A variety of commercial and hydrophobically-modified biocides have been studied. Partition coefficients between octanol and water have been determined at 25° C. by UV/visible absorption. First, the calibration curve of each biocide was determined as optical density ($OD_{abs}$) versus concentration of biocide in $\mu g/g$ (ppm) of water for the predominantly water-soluble materials and $\mu g/g$ of octanol for the predominantly oil-soluble biocides.

A known amount of biocide was placed in a glass vessel containing either 10 ml of water or 10 ml of octanol depending on the solubility of the biocide. An equal volume of the other solvent was added and the glass vessel sealed. The vessel was shaken vigorously for a few minutes and then every few hours for more than 48 hours. Each mixture was placed in a sealed separating funnel and left for a further 24 hours. The water phase of each mixture was removed and the UV/visible spectra run against water with appropriate dilutions to bring absorbance between 0 and 1.5 for the commercial biocides and the octanol fractions were examined for the hydrophobically modified biocides.

The following partition coefficients shown in Table 1 were determined.

TABLE 1

| Biocide | P |
|---|---|
| Promexal ™ | ~4.5 |
| Vantocil ™ | ~0.3 |
| Domiphen ™ | ~50 |
| Kathon ™ | ~1 |
| Proxel ™ | ~0* |
| Compound 1 | >330 |
| Compound 3 | >560 |
| Compound 2 | >130 |
| Compound 4 | >480 |

*i.e. there was almost no biocide in the oil phase.

The log P value of the biocides which are used in the invention must be at least 1.5, preferably at least 2.0.

In use, the aqueous medium is brought into contact with the biocidal material. Different ways of achieving contact include passing the aqueous medium through a container e.g. a column containing the material in particulate form, passing the aqueous medium through a filter of the material and passing the aqueous medium over the material in the form of a surface coating.

The biocidal material is of particular use in photoprocessing systems. Such systems comprise stages for developing, fixing, bleaching and washing an exposed photographic material. Each stage requires apparatus for applying the appropriate aqueous processing solution to the photographic material. The apparatus may comprise means for supplying, removing and, possibly, recirculating such solutions.

The biocidal material may be used to inhibit microbial growth in the wash water or other solutions used in a photoprocessor.

FIG. 1 is a schematic representation of apparatus for use in performing the method of the invention. The apparatus comprises a container 10 having fluid inlet means 11 and fluid outlet means 12 said inlet and outlet means 11, 12 communicating with an inner chamber 13 of the container. When the apparatus is in use, fluid entering the inner chamber through the inlet means 11 flows through the chamber 13 and leaves the container through the outlet means 12. The inner chamber 13 holds a biocidal material in accordance with the invention in the form of particles 14. A filter 15 to retain the particles is positioned at the top of the inner chamber to prevent loss of the particles from the device. The top of the container 10 is provided with plugs 16 (optional) for venting any gas which accumulates in the device.

Fluid entering the device flows down a central tube and subsequently flows up through the particles. The arrows indicate the direction of the flow of fluid through the device.

Figure 2:
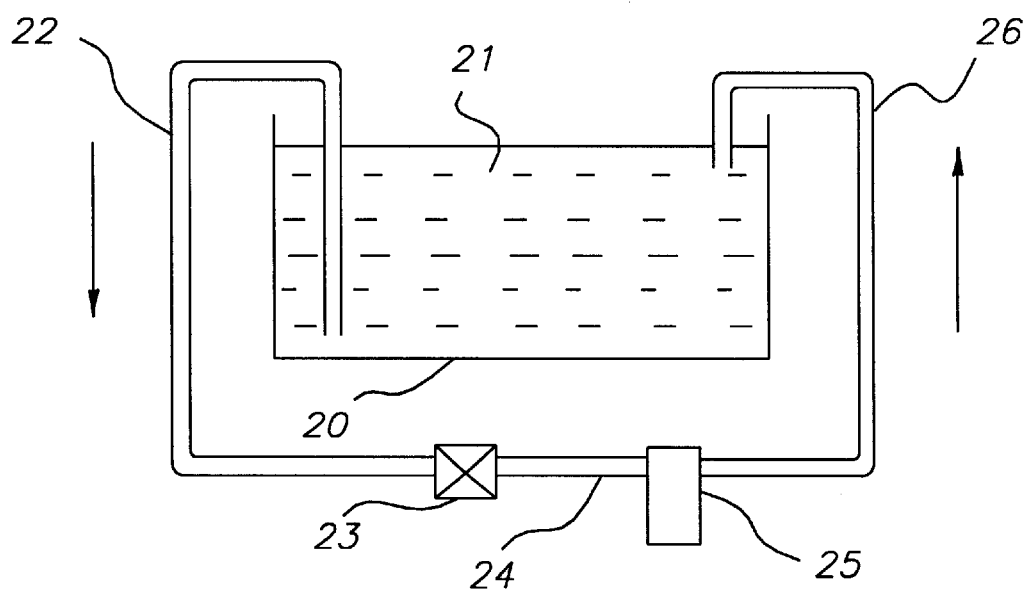
FIG. 2 is a schematic representation of the use of the device shown in FIG. 1.

FIG. 2 is a schematic representation of the use of the apparatus shown in FIG. 1. A tank 20 containing water 21 is shown e.g. the wash water tank of a photoprocessor. Tubing 22 has an open end in the water 21 at the bottom of tank 20, the other end being connected to the inlet of a pump 23 outside the tank 20. Tubing 24 connects the outlet of the pump 23 to the inlet of a device 25 of the type shown in FIG. 1. One end of tubing 26 is connected to the outlet of device 25 and the other end opens into the top of tank 20.

In use, water is pumped from the bottom of tank 20 through device 25 and back into tank 20 in a recirculation loop. The arrows indicate the direction of the flow of water around the loop.

The method of the invention can be applied to an existing biocidal material at any stage of its life. Clearly, it is preferable to practise the invention on a biocidal material which is close to exhaustion and in need of replacement.

The biocidal material may be washed and dried before the biocide is extracted. Extraction occurs by contacting the material with a solvent for the biocide. Any suitable organic solvent may be employed. Examples of suitable solvents include dichloromethane, hexane, heptane, toluene or any water immiscible solvent.

The material may be suspended in the solvent for a period of time with agitation. The suspension may be filtered to remove the dissolved biocide and the filtrate may be subjected to further drying or washing and drying steps. The biocide can be recovered by removal of the solvent e.g. under reduced pressure.

The recovered biocide has been found to be essentially pure with no obvious contaminants.

In accordance with the invention, the extracted biocide is immobilized by hydrophobic exclusion on a support having a hydrophobic surface to produce a new biocidal material.

The support may be a new support. Alternatively, the support of the biocidal material from which the biocide was extracted may be cleaned and re-used.

The invention is further illustrated by way of example as follows.

EXAMPLE 1

Regeneration of the Immobilized Biocide

A device of the type shown in FIG. 1, containing ~300 g immobilized biocide (18.3% w/w 4,5-dichloro-2-n-octylisothiazolin-3-one on a polystyrene resin bead support, Amberlite™ XAD-7HP), that had been running on a recirculation loop attached to stabiliser tank of a Kodak™ 25 paper processor (operating KODAK™ RA-4 processing chemistry) was disconnected after a period of 6.5 weeks continuous use. The container was opened, and the used resin was removed. A portion of the resin (39.74 g) was washed with water (2×50 ml), dried on a sinter funnel, and suspended in dichloromethane (100 ml). The suspension was agitated gently for ~2 hr, and filtered through kieselguhr; the residue was washed with further dichloromethane (2×30 ml). The combined washings and filtrate were dried over magnesium sulphate, and the solvent removed under reduced pressure, to leave the biocide (4,5-dichloro-2-n-octylisothiazolin-3-one) as a pale brown oil (1.95 g) which solidified on standing; analysis (TLC, MS, IR) of the regenerated material showed it to be essentially pure, with no obvious contaminants present. This represented an equivalent final loading of 4.9% or a recovery of 26.8% of unchanged biocide.

The recovered biocide (1.95 g) was dissolved in heptane (50 ml) and fresh Amberlite™ XAD-7HP resin beads (7.80 g), which had been previously washed following the manufacturer's instructions, were added; the mixture was agitated gently for ~10 minutes. The solvent was removed under reduced pressure to leave the regenerated immobilized biocide as pale cream colored active beads (6.71 g).

Microbiological Evaluation

Figure 3:
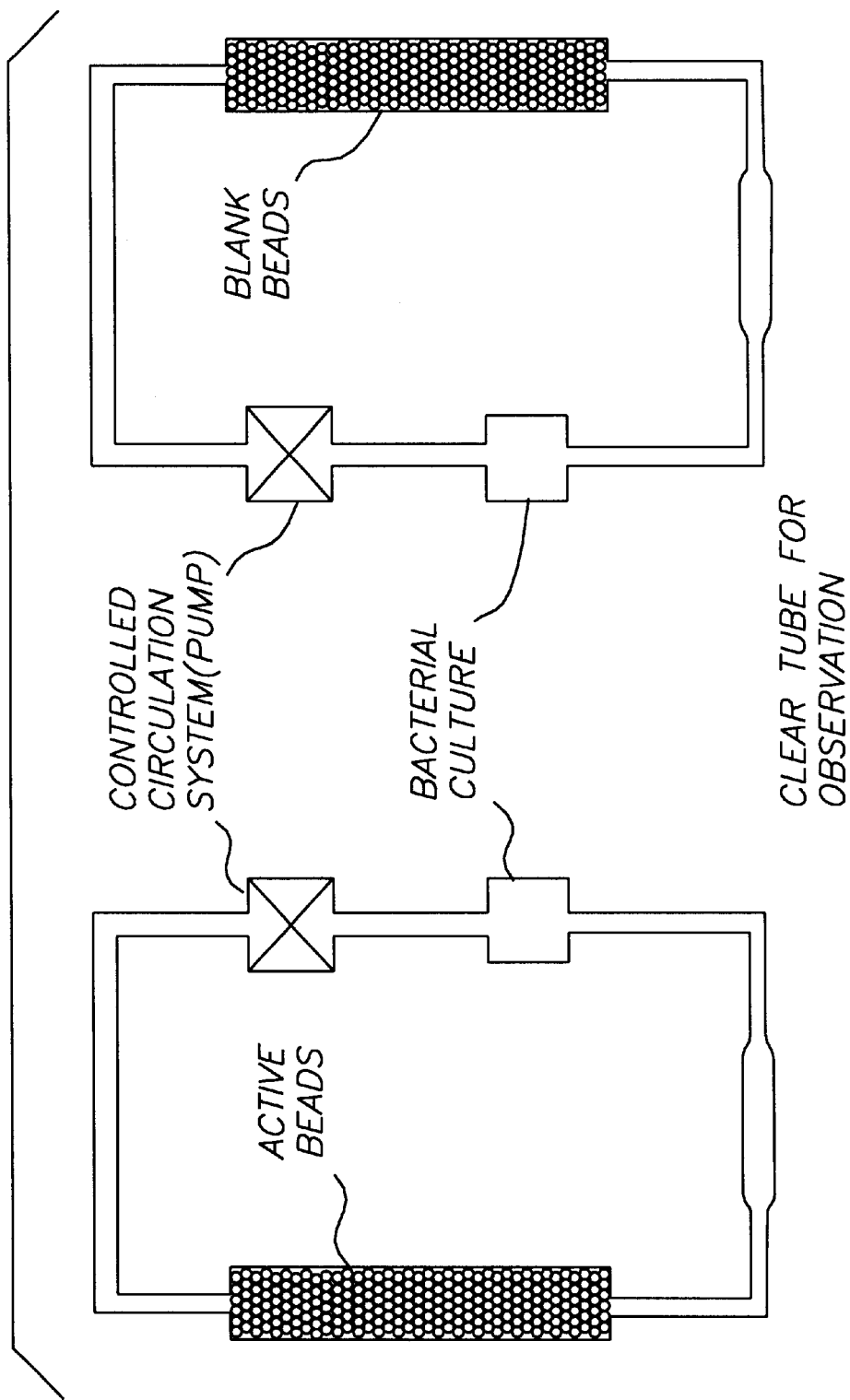
FIG. 3 is a schematic representation of apparatus used in evaluating the performance of the invention.

A control (blank Amberlite™ XAD-7HP), an original (unused) sample of immobilized biocide and the regenerated immobilized biocide were tested in a nutrient broth solution containing approximately $10^4$–$10^5$ bacteria per ml (*Pseudomonas aeruginosa*). The control and active beads were each put in separate 10 cm glass columns with screw-tight plastic adapters and glass nozzles. A nylon mesh, placed between two rubber washers, was used retain the beads within the column. The columns, all silicone rubber tubing and flasks necessary to complete a recirculation loop were sterilized by autoclaving at 120° C. for more than 20 minutes. Each column was placed in a recirculation loop with 50 ml of nutrient broth as illustrated schematically in FIG. 3. A shaking waterbath kept the 250 ml wide-neck round-bottomed conical flasks at 30° C. A small inoculum of pre-prepared bacterial culture was added to each flask. At time zero, a small aliquot of the bacterial culture was removed from each flask to perform initial viable counts and the pumps were started to give a flowrate of 13.5 ml per minute. The bacterial culture flowed up through the beads.

Viable counts (colony forming units[cfu]/ml) were then performed at the time intervals of 0.5, 8 and 24 hours by removing a small aliquot from each flask and performing viable counts.

The results are as follows:

| TIME, hours | Control | Original | Re-immobilized |
|---|---|---|---|
| 0 | 4.83E + 05 | 5.33E + 05 | 8.33E + 04 |
| 0.5 | 3.83E + 04 | 2.67E + 05 | 2.50E + 05 |
| 8 | 3.24E + 03 | 3.30E + 01 | 16 |
| 24 | 1.83E + 08 | 1.60E + 01 | 16 |

Figure 4:
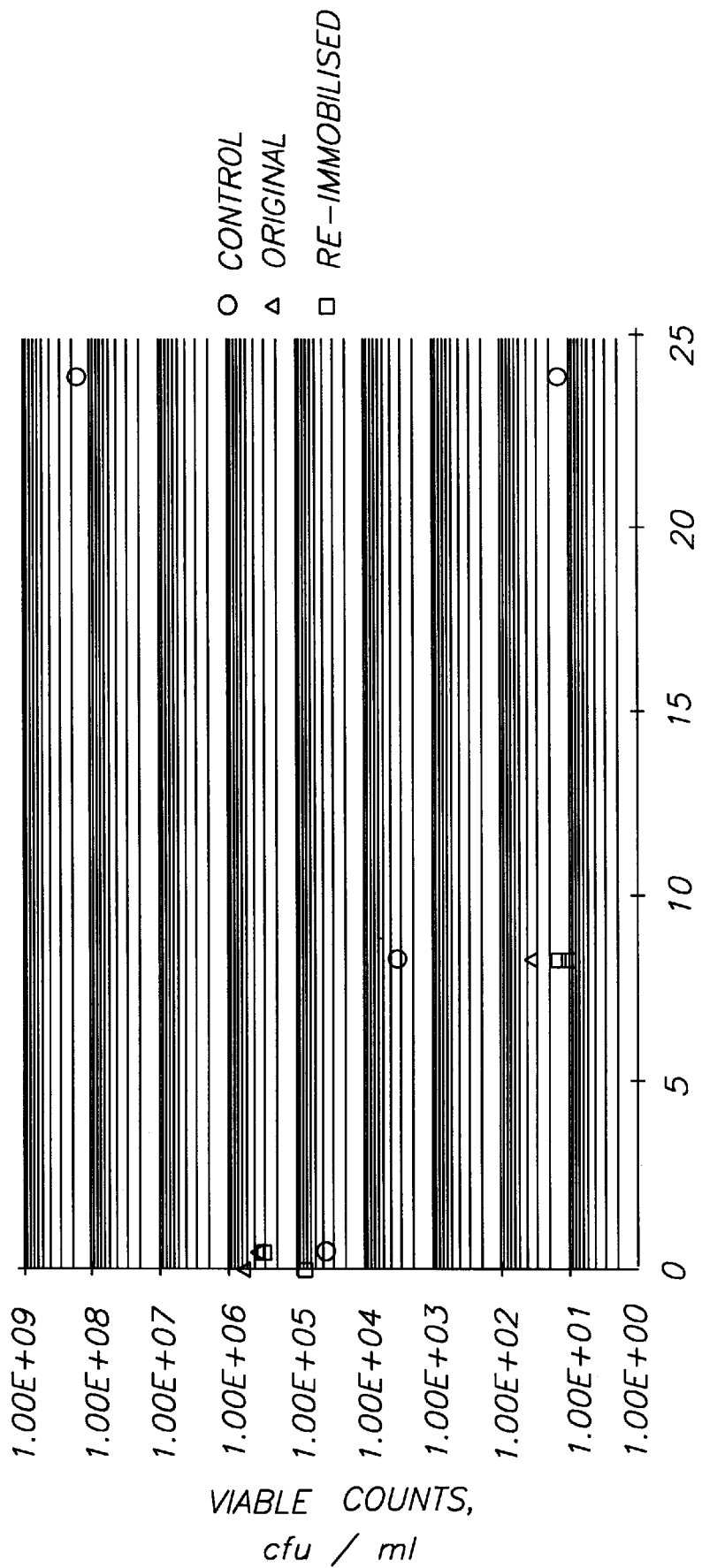
FIG. 4 is a graphical representation of results achieved using a biocidal material obtained by the method of the invention in accordance with Example 1 described hereinafter.

The results are plotted in FIG. 4.

From the results it can be seen that the bacterial population in the active system can no longer be detected after 8 hours, showing a bactericidal effect when compared to the control.

EXAMPLE 2

As Example 1 except that a biocide mixture [19.4% w/w of 4,5-dichloro-2-n-octylisothiazolin-3-one (9%), 5-chloro-2-n-octylisothiazolin-3-one (66%) and 2-n-octylisothiazolin-3-one was (24%)] was used, and the immobilized biocide was packed into a container used in a recirculation loop on the wash tank of a Kodamatic™ 710 graphics processing machine [running KODAK™ RA2000 (1+2) developer and KODAK™ Fixer 3000 (1+3)].

The device was removed after 4 weeks continuous use; a portion of the recovered resin (50 g) was suspended in dichloromethane (200 ml) and stirred for 24 hr. The suspension was filtered and the filtrate was washed with water (100 ml), dried with magnesium sulphate and evaporated under reduced pressure to leave the recovered biocide mixture as a brown oil (3.22 g). Analysis (TLC, IR, MS) showed the recovered material to be essentially identical to the originally immobilized mixture. This represented an equivalent final loading of 6.4%, or a recovery of 33.0% of unchanged biocide.

What is claimed is:

1. A method of preparing a biocidal material which comprises taking a biocidal material comprising a biocide having a log P value of at least 1.5 immobilized by hydrophobic exclusion on a support having a hydrophobic surface which has been used for inhibiting microbial growth in an aqueous medium, extracting the biocide from the biocidal material with a solvent, and immobilizing the extracted biocide by hydrophobic exclusion on a support having a hydrophobic surface.

2. A method according to claim 1 wherein the biocide has the structure

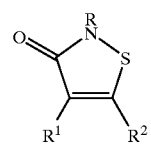

wherein
R represents hydrogen, alkyl, aryl, alkaryl and aralkyl; and,
$R^1$ and $R^2$ independently represent hydrogen, halogen, alkyl, or $R^1$ and $R^2$ taken together represent the atoms necessary to complete a fused carbocyclic ring.

3. A method according to claim 1 wherein the biocide has the structure

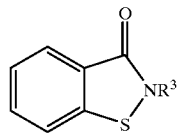

wherein $R^3$ is an alkyl group having from 4 to 20 carbon atoms or an aryl group having from 6 to 20 carbon atoms.

4. A method according to claim 1 wherein the biocide has the structure

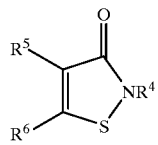

wherein $R^4$ is an alkyl group having from 5 to 20 carbon atoms; and, $R^5$ and $R^6$ are selected from hydrogen and halogen.

5. A method according to claim 1 wherein the biocide has the structure

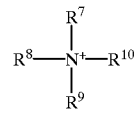

wherein each of $R^7$, $R^8$ and $R^9$ is hydrogen or an alkyl group providing a total of from 2 to 20 carbon atoms;

$R^{10}$ is a substituted or unsubstituted alkyl or aryl group; and,

Y is a counter anion.

6. A method according to any one of the preceding claims wherein the biocide has a log P value of at least 2.

7. A method according to claim 1 wherein the support is a hydrophobic polymer.

8. A method according to claim 7 wherein the support is in the form of polymer beads.

9. A method according to claim 7 wherein the support is porous.

10. A method according to claim 1 wherein the solvent is a water immiscible solvent.

* * * * *